(12) United States Patent
Hubbell et al.

(10) Patent No.: US 6,539,780 B2
(45) Date of Patent: Apr. 1, 2003

(54) SELF-COMPENSATING TENSIOMETER AND METHOD

(75) Inventors: Joel M. Hubbell, Idaho Falls, ID (US); James B. Sisson, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/792,124

(22) Filed: Feb. 22, 2001

(65) Prior Publication Data

US 2002/0112531 A1 Aug. 22, 2002

(51) Int. Cl.⁷ .............................................. E21B 49/08
(52) U.S. Cl. ..................... 73/73; 73/152.51; 73/152.46; 73/152.55
(58) Field of Search .................... 73/73, 152.51, 73/152.55, 152.46

(56) References Cited

U.S. PATENT DOCUMENTS

| | | | | |
|---|---|---|---|---|
| 4,453,401 A | * | 6/1984 | Sidey | 73/73 |
| 5,337,601 A | * | 8/1994 | Becker et al. | 340/949 |
| 5,644,947 A | | 7/1997 | Hubbell et al. | 73/73 |
| 5,758,538 A | | 6/1998 | Hubbell et al. | 73/73 |
| 5,915,476 A | | 6/1999 | Hubbell et al. | 166/113 |
| 5,969,242 A | * | 10/1999 | Hubbell et al. | 166/250.03 |

* cited by examiner

Primary Examiner—Daniel S. Larkin
Assistant Examiner—André K. Jackson
(74) Attorney, Agent, or Firm—Alan D. Kirsch

(57) ABSTRACT

A pressure self-compensating tensiometer and method to in situ determine below grade soil moisture potential of earthen soil independent of changes in the volume of water contained within the tensiometer chamber, comprising a body having first and second ends, a porous material defining the first body end, a liquid within the body, a transducer housing submerged in the liquid such that a transducer sensor within the housing is kept below the working fluid level in the tensiometer and in fluid contact with the liquid and the ambient atmosphere.

10 Claims, 5 Drawing Sheets

SELF-COMPENSATING TENSIOMETER AND METHOD

CONTRACTUAL ORIGIN OF THE INVENTION

This invention was made with United States Government support under Contract No. DE-AC07-99ID13727 awarded by the United States Department of Energy. The United States Government has certain rights in the invention.

BACKGROUND OF THE INVENTION

This invention relates to tensiometers for measuring soil water potential and more specifically to a tensiometer that self-compensates to changing water levels and pressures in the tensiometer reservoir, thereby permitting longer useful operating periods.

The use of tensiometers for monitoring moisture potential in soil is known. For example, our invention claimed in U.S. Pat. Nos. 5,644,947 and 5,915,476 (which are hereby incorporated by reference) describe portable tensiometers for monitoring moisture potential in soil. As can be seen in FIG. 2 of the '947, the tensiometer has a transducer 30 mounted externally to, and in fluid communication with, a fluid chamber 26. Because the transducer of '947 is mounted externally, a disadvantage of the '947 patent is that the pressure measured by the transducer is subject to changes in both the water level within the chamber as well as the changing air pressure of the headspace above the water level within the chamber. Also, the amount of water that can be contained within the chamber of the '947 invention is limited by the length of the column of water in the water chamber thereby restricting the operating period of the tensiometer. The invention disclosed '947 has the pressure sensor on the top of the instrument to measure the soil water potential in the adjacent sediment. The pressure sensor is located on the top of the instrument for ease of connection and to reduce the overall size (diameter) since it is vertically oriented to be placed in a borehole.

It is an object of the present invention to provide a tensiometer that automatically corrects the pressure measurement so that decreasing water levels within the tensiometer do not affect the recorded pressure measurements.

It is another object of the present invention to provide a tensiometer capable of longer operation periods as a result of its increased water volume capacity.

It is still a further object of the present invention to provide a tensiometer that will record pressure changes relative to atmospheric pressure and is independent of changes in water level within the tensiometer.

SUMMARY OF THE INVENTION

To achieve the foregoing and other objects, the present invention provides a self-compensating tensiometer that measures the total head in the system (i.e., the pressure head and the water level elevation head). In one preferred embodiment the self-compensating tensiometer comprises a body having a porous cap at one end and a chamber filled with liquid within the body. A pressure transducer housing contains a transducer sensor, the housing being immersed within the liquid. A first side of the transducer housing being in fluid communication with the liquid contained within the tensiometer housing. A second side of the transducer housing is vented through a reference port and vent tube to the atmosphere (either at the earth surface or the ambient atmosphere within the bore hole). In another embodiment of the invention, the transducer housing, reference port and portion of the reference vent tube are embedded in substantially solidified material (for example epoxy) to stabilize these components within the tensiometer. In this embodiment, a portion of the transducer housing may extend beyond the stabilizing material to provide fluid communication with the liquid within the tensiometer, or alternatively fluid communication means could be provided through an opening provided in the stabilizing material. A method for utilizing the self-compensating tensiometer is also claimed.

BRIEF DESCRIPTION OF THE DRAWINGS

The present invention is illustrated in the accompanying drawings where.

DETAILED DESCRIPTION OF THE INVENTION

Figure 1:
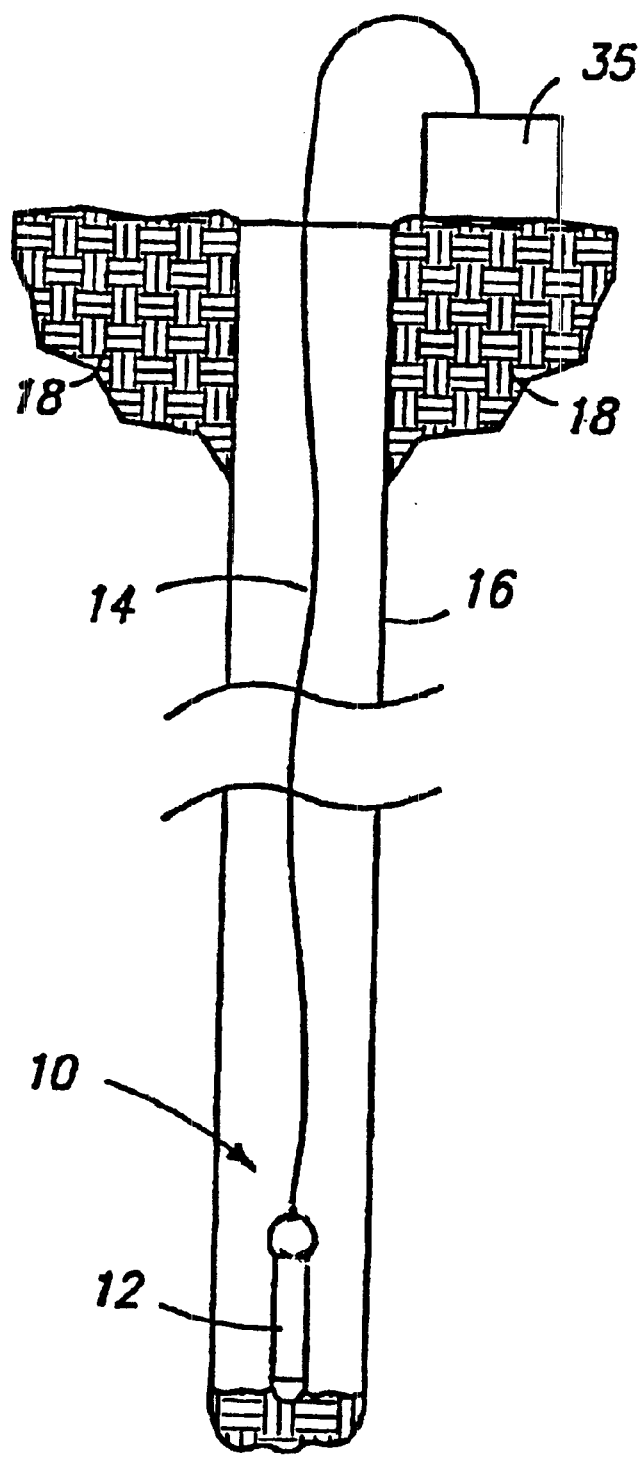
FIG. 1 is a diagrammatic representation of a tensiometer apparatus positioned within a borehole for measurement in accordance with the present invention.

Referring to FIG. 1 a diagrammatic representation of a tensiometer apparatus 10 is shown positioned in a borehole. Tensiometer apparatus 10 comprises a body 12 and flexible suspension line 14. Line 14 is utilized to raise and lower body 12 relative to a bore hole 16 provided within earthen soil 18. A data logger 35 which records the data transmitted from the tensiometer apparatus is shown on the surface of the earth. The pressure sensor and wire that connects to the data logger is not shown in this figure. The artisan will recognize utility of the devices and methods disclosed herein with other earthen openings, such as trenches and exposed earthen faces.

Figure 2:
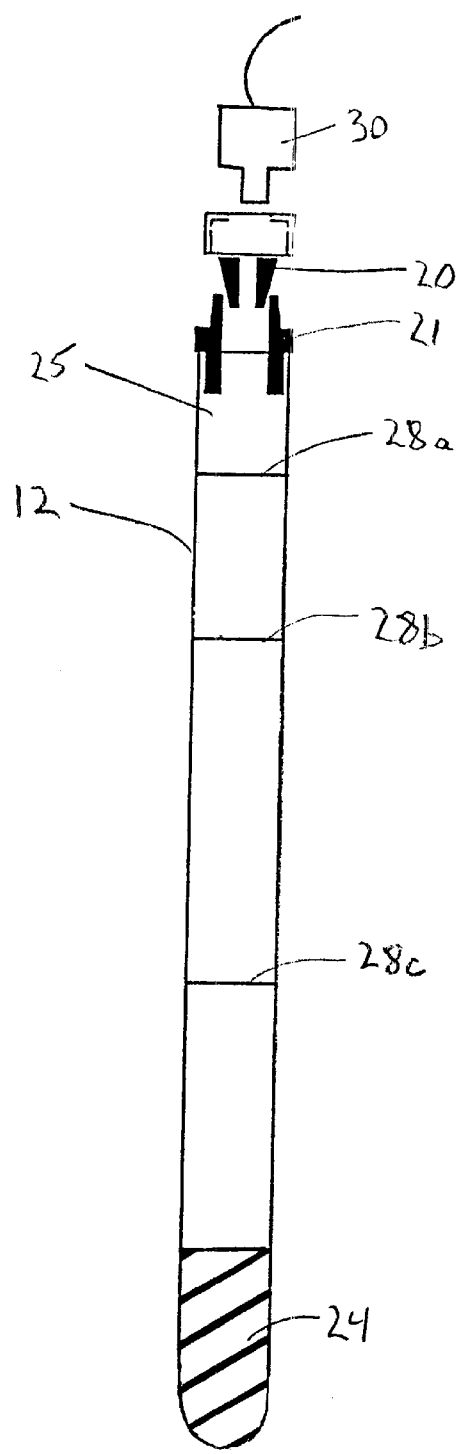
FIG. 2 is a simplified diagrammatic view of a prior art tensiometer.

A diagrammatic drawing of a conventional tensiometer, such as the tensiometer of '947, is shown in FIG 2. As can be seen in FIG. 2, the transducer 30 is mounted externally to the sealed body 12. Air tight connectors 20 and 21 provide the means for sealing the body 12. The tensiometer has a porous cup 24 and one end of the body and in physical contact with the soil. Various water levels are shown in FIG. 2 represented as 28a, 28b, and 28c. Headspace 25 is shown as the volume between the water level and within the sealed body. The pressure sensing portion of the instrument shown in FIG. 2 has a column of water in the device and over time air accumulates above the water in the chamber (trapped in the top of the device). The instrument is originally filled completely with water but air accumulates in the device in normal operation and the water level declines in this chamber over time. This decline in the water level affects the measurements obtained by a pressure sensor located above the water column. As can be seen from FIG. 2, the pressure measured by transducer sensor (not shown) contained within transducer housing 30 is a function of both the air pressure within the headspace 25 and the pressure due to the changing water level. An alternative tensiometer disclosed in '947 contemplates mounting the transducer internally within the headspace of the body. (See '947 column 4, lines 39–41).

Such alternative mounting within the headspace would likewise suffer the disadvantage of measuring pressure as a function of both the air pressure and pressure changes due to changes in the water level within the reservoir.

Figure 3:
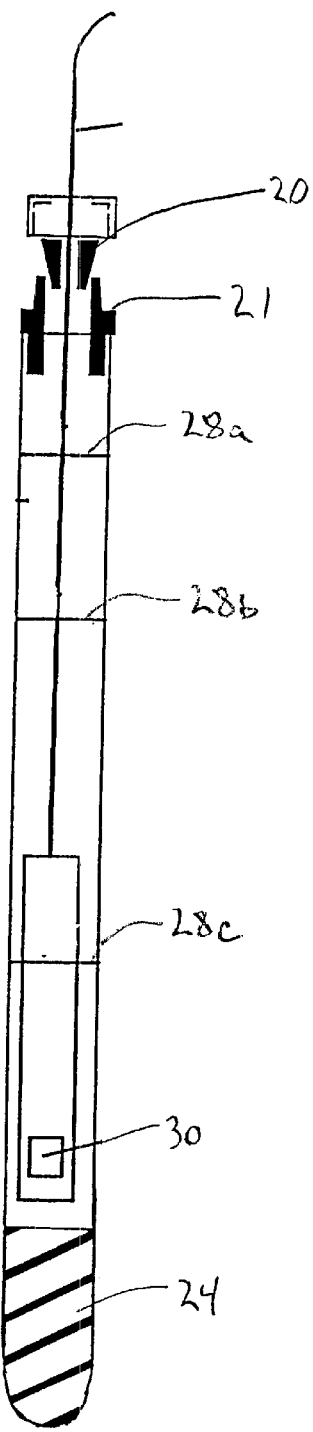
FIG. 3 is a simplified diagrammatic view of the tensiometer in accordance with the present invention.

Referring now to FIG. 3 a diagrammatic view of the self-compensating tensiometer of the present invention is shown. The self-compensating transducer comprises a body 12 having first and second ends, the first body end having a porous cup 24. Various water levels are also shown in FIG. 3 represented as 28a, 28b and 28c. In the self-compensating transducer the transducer housing is below the various water levels such that the pressure measurement side of the immersed transducer housing is open to the water contained with the body 12 while, as more fully described below, the other end of the transducer housing (reference port) is vented to the atmosphere or to the soil gas a short distance above the measurement depth (porous cup 24) of the tensiometer (See FIG. 4). A absolute pressure transducer may also be substituted for the transducer described above. By immersing the transducer housing in the water, the transducer measures the pressure within the body 12 independent of changes in the water level. To describe how this lowering of the water level effects measurements recorded by a pressure sensor it is assumed for the following example, that the soil water potential in the surrounding sediment does not change over time. In the instruments original water filled situation, and once the pressure in the instrument has equilibrated with the soil water potential in the device, the sensor is sensing the combination of the negative pressure from the hanging water column in the device and the water potential as reflected as a negative pressure, relative to atmospheric pressure. As the water level declines inside the instrument, allowing more air to enter, the total water potential pressure is the same but the hanging water column has declined. If the water level in the tensiometer declines, for example, the equivalent pressure of 20 cm of water the sensor would provide a measurement that is equivalent to the pressure in the soil with the addition of the equivalent pressure of 20 cm of water. Thus, if the water potential was −100 cm pressure, the apparent pressure from the sensor would be −80 cm. Since the rate of accumulation of air into the device cannot be predicted in advance of operation of the instrument, the change in measurements from actual readings cannot be predicted. It then follows that increasing the water filled length of the device and allowing the instrument to operate (accumulating air) for extended time period will introduce more error into the measurements.

The pressure sensor in the self-compensating tensiometer is located beneath the operational water level of the tensiometer. The sensor then senses the negative pressure from the hanging water column (which does not change), and the combination of the pressure of the water and the pressure of the air above sensor. If the water potential is constant, as the water level in the device changes the air pressure changes to reflect this pressure change. As long as the measurement depth of the sensor is covered by water, the sensor will obtain measurements reflective of the true water potential in the adjacent material.

Figure 4:
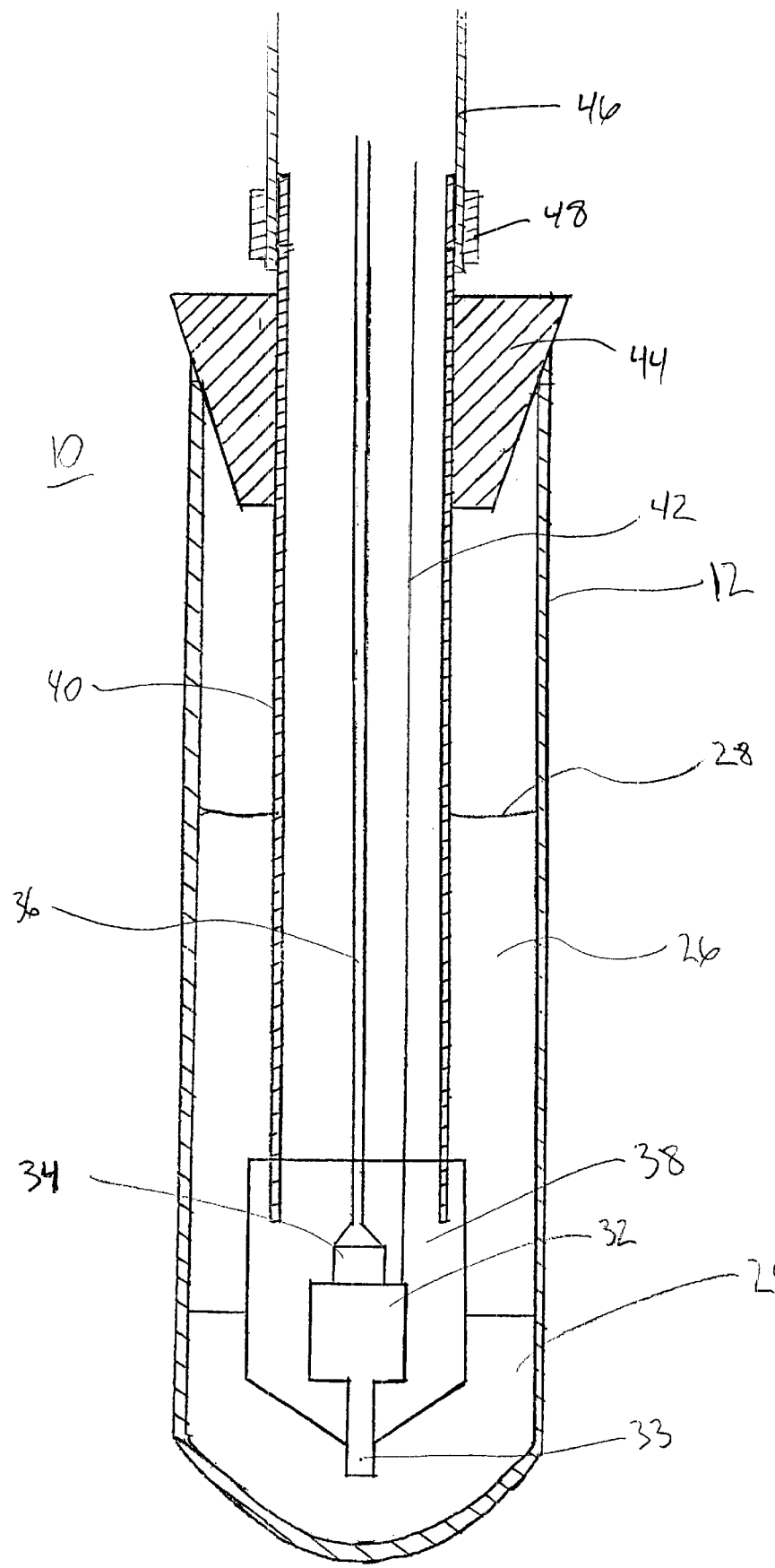
FIG. 4 is an enlarged side sectional view of a portion of the tensiometer of the present inventions showing the transducer housing immersed below of the water level contained with the transducer chamber.

FIG. 4 shows an enlarged sectional view of the self-compensating transducer of the present invention. The self-compensating transducer comprises a body 12 having first and second ends, the end being a porous cup 24. Within the body 12 and proximate to the first body end is the transducer housing 32. The transducer housing 32 is contained within a sealed nose cone 38 which is positioned below the water level 28. Preferably the entire nose cone 38 is filled with epoxy to encapsulate and protect the transducer housing and connections. Alternately as described below with reference to FIG. 5, the nose cone can be omitted, the transducer apparatus 32, 34, 36, and 32 placed in the rigid tubing 40 and the transducer apparatus encapsulated with epoxy with the port 33 in fluid communication with the fluid of the tensiometer. The transducer sensor (not shown) is contained within the transducer housing 32. The nose cone is attached to a rigid tubing 40. Preferably rigid tubing 40 is PVC tubing, however other types of impermeable tubing could also be utilized (i.e. stainless steel, brass, plastic). The transducer housing 32 has a first end 33 that is in fluid contact with the degassed water 26. Wire leads 42 which extend from the transducer sensor/housing to the data logger 35 (in FIG. 1) are also shown.

Attached to the transducer housing 32 second end is a reference port 34 that further connects to a reference vent tube 36. Reference vent tube 36 is a small diameter tubing that can extend beyond the rigid tubing 40 and into the tubing that extends to land surface 46. Tubing 46 can be flexible semi-rigid tubing or rigid tubing and attached to rigid tube 40 by several methods such as band 48 shown in FIG. 4. Its purpose is to raise and lower the pressure sensor and allow downward pressure to be applied to the sensor to seal the device. Reference vent tube 36 is attached to the reference port 34 via heat shrink tubing or other sealable means. The reference vent tube 36 vents the second end of the transducer sensor to the atmosphere.

Accordingly the transducer measures the pressure caused by the water within the body as a function of atmospheric pressure. Since the self-compensating tensiometer measurements are not affected by the height (length) of the water reservoir, the reservoir can be lengthened to allow more water to be contained within the tensiometer reservoir. In other words, the volume of water used can be increased without increasing the diameter of the tensiometer. Increasing the diameter of the tensiometer is to be avoided because of limited bore hole diameter and the potential of having other instruments in the bore hole. A larger water volume correlates to a longer operation time between refilling with water, thereby significantly increasing the time between maintenance. It is estimated the self-compensating tensiometer can hold enough water to permit an operational time period of over one year.

Figure 5:
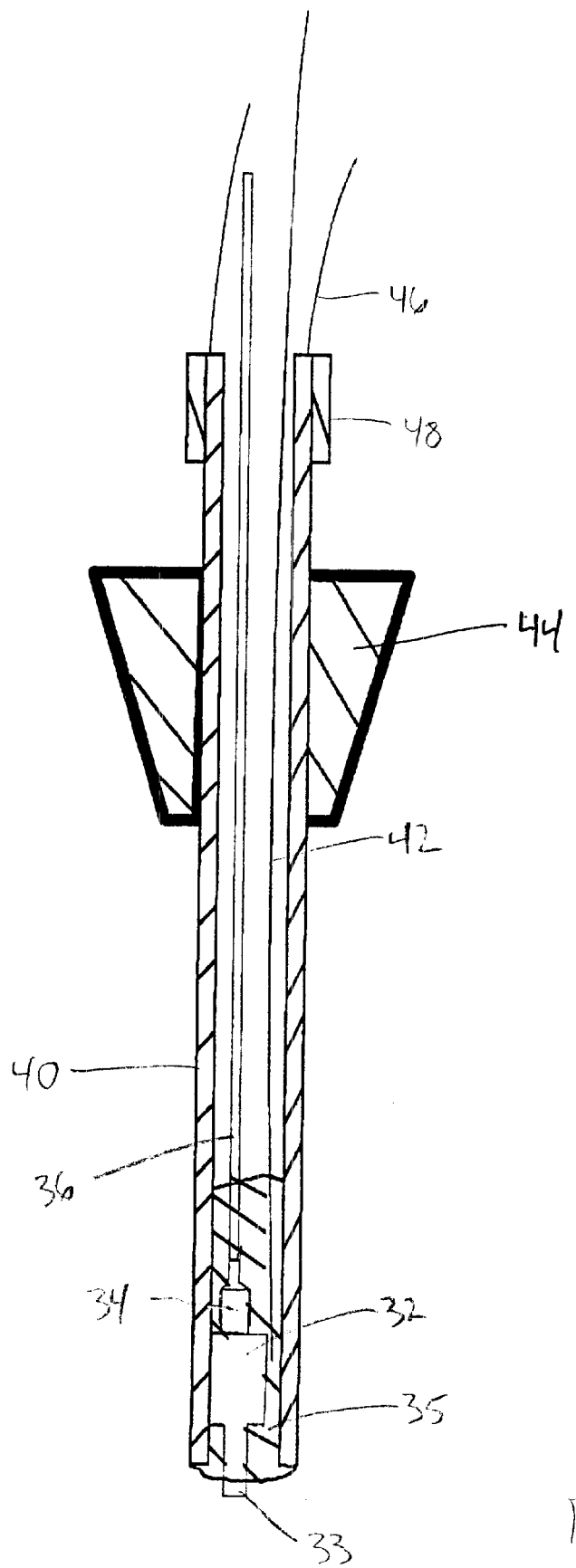
FIG. 5 is an enlarged side sectional view of a portion of the tensiometer of the present invention showing the transducer, wiring and vent tube encapsulated in solid material such as an epoxy.

FIG. 5 shows an enlarged sectional view of the self-compensating transducer of the present invention. In this figure the transducer apparatus 32, 34, and 36 are placed in the rigid tubing 40 and the transducer apparatus encapsulated within a solidified material, such as epoxy, with the port 33 in fluid communication with the fluid of the tensiometer.

Figure 6:
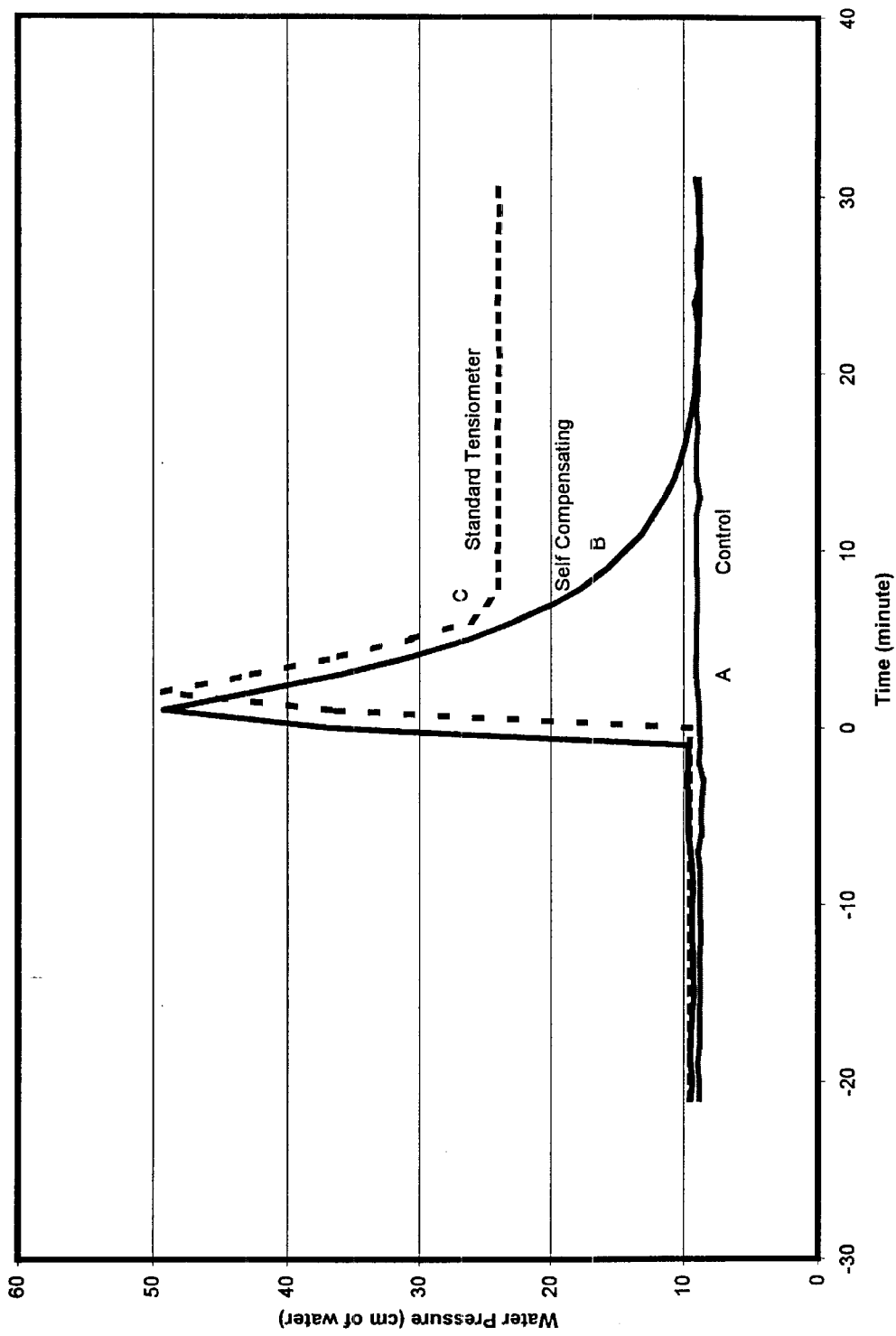
FIG. 6 is a table showing water pressure as a function of time for the self-compensating tensiometer of the present invention, a conventional tensiometer and a control tensiometer.

FIG. 6 shows the water level response from three portable advanced tensiometers where one is a control, the second is a standard tensiometer and the third is a self-compensating portable tensiometer. The instruments have been placed in a beaker with a known depth of water and all three of the instruments referenced to read about 8 cm of water pressure in the data logger. Instrument (A) is a control with the water level in the instrument staying steady over the entire test. This instrument shows the normal variations of measurements over time for the pressure sensors used in the test. The self compensating tensiometer (B), shows the response from opening the tensiometer at time zero and lowering the water level inside the instrument about 15 cm, sealing the chamber (resulting in an increase in pressure in the apparent reading) and placing the tensiometer back in the beaker of water with the same depth of water. The sensor returns to the original reading plus or minus 1 cm of water, within 20 minutes of the perturbation of pressure, showing that the measurement is not affected by changes in the water level inside of the tensiometer. This indicates that the device works as intended and that the measurement is not affected by the water level inside the tensiometer. The third instrument (C) shows the response of a standard portable tensiometer with the pressure sensor located above the water reservoir (as shown in FIG. 2). As with the self-compensating tensiometer, the instrument is opened, the water level in the instrument lowered about 15 cm and the instrument resealed and placed in the beaker of water at the original depth. The water pressure inside the tensiometer builds up due to the sealing of the tensiometer and then the pressure decreases. The pressure does not approach the original measurement (8 cm of water) but rather is 15 cm higher when the measurements equilibrate. This is because the length of the hanging water column in the tensiometer is 15 cm lower and so this hanging water column does not exert this downward (negative) pressure on the sensor. Thus, a change in the water level within a standard tensiometer with at transducer above the water level will change the readings from the pressure sensor in the tensiometer. Since tensiometers lose water over time so that the water level in the instrument change, this affects the overall accuracy of the instrument. Removing this source of error in the measurement improves the accuracy of the instrument.

As can be seen in FIG. 6, after water is removed from the self-compensating tensiometer reservoir the water pressure of the self-compensating tensiometer return to the control level of an tensiometer having constant water pressure. The upward spike in the data is a response of sealing the instrument, thereby temporarily increasing the pressure in the chamber. However, it has been observed that a conventional tensiometer would remain at an elevated water pressure after water has been removed from the reservoir. Accordingly, for a conventional tensiometer the reading would have to be corrected as the water level declines in the tensiometer during normal use and since the water level decline may not be predictable or linear this detrimentally affects the accuracy of the tensiometer pressure readings.

We claim:

1. A pressure self-compensating tensiometer to in situ determine below-grade soil moisture potential of earthen soil within a bore hole, comprising:
   a body having opposite first and second ends and being adapted for complete insertion into earthen soil below grade;
   a porous cup material provided at the first body end, the porous material at least in part defining a fluid chamber within the body at the first end;
   a liquid received within the fluid chamber;
   a pressure transducer mounted within a transducer housing, the transducer housing having first and second ends and being immersed within the liquid; the transducer housing first end being opened to the liquid; and
   a reference port connected between the transducer housing's second end and a reference vent tube, the reference vent tube venting to the atmosphere.

2. The tensiometer of claim 1 further comprising suspension means connected to the body adjacent the second body end, the suspension means being of sufficient strength to gravitationally freely self suspend the self-compensating tensiometer and to lower the transducer down the bore hole such that the porous material contacts the earthen soil within the bore hole.

3. The tensiometer of claim 2 wherein the suspension means is a flexible tube.

4. The tensiometer of claim 1 wherein the pressure transducer is encapsulated, but for the first housing end, in a solid material to stabilize the transducer housing within the body.

5. The tensiometer of claim 4 wherein the solid material is an epoxy.

6. A pressure self-compensating tensiometer to in situ determine below-grade soil moisture potential of earthen soil within a bore hole, comprising:
   a body having opposite first and second ends and being adapted for complete insertion into earthen soil below grade;
   a porous cup material provided at the first body end, the porous material at least in part defining a fluid chamber within the body at the first end;
   a liquid received within the fluid chamber;
   a pressure transducer mounted within a transducer housing, the transducer housing's having first and second ends; the transducer housing first end in fluid communication with the liquid;
   a reference port connected between the transducer housing's second end and a reference vent tube, the reference vent tube venting to the atmosphere; and
   a solid material substantially encapsulating the transducer housing except for the transducer housing first end to stabilize the pressure transducer and housing.

7. The tensiometer of claim 6 further comprising suspension means connected to the body adjacent the second body end, the suspension means being of sufficiently strength to gravitationally freely self suspend the self-compensating tensiometer and to lower the transducer down the bore hole such that the porous material contacts the earthen soil within the bore hole.

8. The tensiometer of claim 6 wherein the suspension means is a flexible tube.

9. The tensiometer of claim 6 wherein the solid material is an epoxy.

10. A method of monitoring soil moisture potential in below-grade earth soil comprising:
   providing a body having opposite first and second ends, a porous material provided at the first body end, the porous material at least in part defining a fluid chamber with the body at the first end, the fluid chamber being fluidicially sealed within the body, but for the porous material, a liquid received within the fluid chamber, a pressure transducer within a housing, the housing contained within the fluid chamber and submerged in the liquid such that one end of the transducer is in fluid communication with the liquid and an opposite end of the transducer is vented to the atmosphere,
   lowering the body, transducer and liquid below grade into an opening provided in earthen soil until the porous material reaches and contacts earthen soil;
   permitting the liquid to permeate to the porous material to cause a change in pressure in the fluid chamber;
   determining the change in pressure with the pressure transducer relative to atmospheric pressure and independent of amount of liquid.

* * * * *